United States Patent [19]

Kiefer et al.

[11] Patent Number: 4,605,763

[45] Date of Patent: Aug. 12, 1986

[54] PROCESS FOR THE PURIFICATION OF TEREPHTHALIC ACID

[75] Inventors: Judy E. Kiefer; William V. Phillips; Thomas E. Woodruff, all of Kingsport, Tenn.

[73] Assignee: Eastman Kodak Company, Rochester, N.Y.

[21] Appl. No.: 646,196

[22] Filed: Aug. 31, 1984

[51] Int. Cl.$^4$ .............................................. C07C 51/42
[52] U.S. Cl. ............................ 562/487; 562/412; 562/485
[58] Field of Search .............................. 560/485, 487

[56] References Cited

U.S. PATENT DOCUMENTS

| | | | |
|---|---|---|---|
| 3,431,296 | 3/1969 | Ichikawa et al. | 562/487 |
| 3,644,507 | 2/1972 | Witt et al. | 562/487 X |
| 3,717,674 | 2/1973 | Blay | 562/487 X |
| 4,201,871 | 5/1980 | Tanouchi et al. | 562/486 |
| 4,314,073 | 2/1982 | Crooks | 562/487 X |
| 4,447,646 | 5/1984 | Johnson et al. | 562/487 |

*Primary Examiner*—Natalie Trousof
*Assistant Examiner*—Vera C. Clarke
*Attorney, Agent, or Firm*—Clyde L. Tootle; David E. Cotey; J. Frederick Thomsen

[57] ABSTRACT

The present invention provides an improved process for the purification of crude terephthalic acid which has been produced by the oxidation of para-xylene. The process comprises contacting the crude terephthalic acid with oxygen-containing gas at a temperature of about 190° to 230° C. and a pressure of about 1500 to 3600 kPa in the presence of a solvent comprising an alkanoic acid which is preferably acetic acid. The process further comprises the use of a novel and surprisingly effective catalyst system. The catalyst system comprises cobalt, a bromine source, and pyridine.

20 Claims, No Drawings

PROCESS FOR THE PURIFICATION OF TEREPHTHALIC ACID

BACKGROUND OF THE INVENTION

The present invention relates to an improved process for the purification of crude terephthalic acid. More particularly, the invention relates to a novel process for recovering terephthalic acid of improved purity from a suspension containing crude terephthalic acid. The crude terephthalic acid is obtained by the liquid phase oxidation of parasubstituted aromatic compounds in the presence of oxidizing catalyst.

In typical known processes for producing terephthalic acid, a para-substituted aromatic compound is oxidized to the desired acid. Such compounds include p-toluic acid, p-tolualdehyde, para-dialkylbenzenes, etc. A preferred dialkylbenzene is para-xylene. The following discussion is directed to the oxidation of para-xylene as an example of such prior art oxidation processes. In the typical oxidation of para-xylene, the oxidation is conducted in acetic acid solvent with molecular oxygen in the presence of a catalyst. The catalyst generally used is a cobalt compound and a manganese compound. An oxidation promoter such as a bromine compound, methyl ethyl ketone, paraldehyde, or acetaldehyde is occasionally used. When para-xylene is oxidized in the liquid phase in acetic acid and in the presence of a catalyst, the product terephthalic acid, being very difficultly soluble in acetic acid, crystallizes out of the solvent acetic acid, forming a suspension. The suspending medium, that is, the acetic acid, contains a small amount of terephthalic acid dissolved therein, catalyst, unreacted para-xylene, intermediate oxidation products such as para-tolualdehyde, para-toluic acid, 4-carboxybenzaldehyde, and other organic impurities which may cause discoloration.

In order to reduce the concentration of such impurities in the solid product, the crude terephthalic acid is generally subjected to a further purification treatment. One such treatment which has been known in the art involves heating the crude terephthalic acid with acetic acid, propionic acid, or butyric acid until it is dissolved, and then cooling the solution to crystallize the terephthalic acid.

Another purification process is disclosed in U.S. Pat. No. 3,431,296. This process involves contacting a suspension composed of 6 to 100 parts by weight of crude terephthalic acid in 100 parts by weight of an aliphatic monocarboxylic acid of 2 to 4 carbon atoms (or a defined aqueous solution thereof) with molecular oxygen-containing gas at 180° to 230° C. in the presence of a cobalt compound. This patent does not contemplate the use of any additional catalyst components.

Other disclosures, e.g., U.S. Pat. No. 4,314,073, U.S. Pat. No. 4,201,871, and Japanese Kokai No. 135,939/74 teach purification processes involving secondary or continuing oxidations (such as that discussed immediately above) wherein the mother liquor from the primary oxidation stage is displaced or diluted by fresh acetic acid. Such secondary and/or continuing oxidations typically utilize catalyst systems comprising cobalt, manganese, and/or bromine components.

U.S. Pat. No. 4,447,646 discloses a purification of crude terephthalic acid which is characterized by the use of a secondary oxidation stage which utilizes a catalyst system comprising cobalt, a bromine compound, and samarium.

It has now been found that the purification of crude terephthalic acid which is produced by the oxidation of para-substituted aromatic compounds can conveniently be accomplished by employing a secondary oxidation stage which utilizes a catalyst system comprising cobalt, a bromine source, and pyridine.

SUMMARY OF THE INVENTION

The present invention provides an improvement in a process for the purification of crude terephthalic acid, the purification process comprising contacting crude terephthalic acid with oxygen-containing gas at elevated temperature and pressure in the presence of a solvent comprising at least one lower alkanoic acid and a catalyst system comprising cobalt. The improvement comprises employing in the catalyst system a bromine source and pyridine.

DETAILED DESCRIPTION OF THE INVENTION

The present invention provides an improved process for the purification of crude terephthalic acid. The crude terephthalic acid which is utilized in the process of the present invention is obtained by the oxidation of para-substituted aromatic componds (e.g., p-xylene). The oxidation of such compounds to crude terephthalic acid is well known in the art, and any known procedures for accomplishing the primary oxidation can be employed. However, the process of the present invention is most advantageously practiced in conjunction with a primary oxidation which employs a lower alkanoic acid (i.e., alkanoic acid having 2 to 4 carbon atoms; e.g., acetic acid) and which employs a catalyst system comprising cobalt and a bromine compound. Other known processes involve the use of additional catalyst components, such as manganese.

The purification process of the present invention involves the secondary oxidation of the crude terephthalic acid produced in a primary oxidation, such as that described above.

The purification process comprises contacting the crude terephthalic acid with oxygen-containing gas. Preferred oxygen-containing gases include air and other mixtures of nitrogen and oxygen. One such convenient mixture which can be used in the process of the present invention is the vent gas from the primary oxidation which ordinarily comprises about 5 to 20% oxygen.

The crude terephthalic acid is contacted with the oxygen-containing gas at elevated temperature and pressure. The purification process is preferably conducted at relatively low temperatures of about 190° to 230° C. The purification is preferably conducted at a pressure of 1500 to 3600 kPa (about 200 to 500 psig).

The purification process of the present invention is conducted in the presence of a solvent comprising at least one lower alkanoic acid. By "lower alkanoic acid" is meant alkanoic acids having 2 to 4 carbon atoms. A preferred lower alkanoic acid is acetic acid. In especially preferred embodiments, the solvent comprises a mixture of water and acetic acid which has a water content of about 5% by weight. The solvent is conveniently and preferably obtained by displacing about 80 to 90% of the mother liquor from the primary oxidation with fresh, wet acetic acid containing about 5% water. The exchange may be accomplished in any convenient apparatus but can perhaps most easily be accomplished in a centrifuging apparatus, such as one or more cyclones.

The purification process of the present invention is conducted in the presence of a catalyst system which comprises cobalt. The catalyst system further comprises a bromine source and pyridine. Additional catalyst components are not necessary to the practice of the present invention.

The residual mother liquor from the primary oxidation supplies the necessary cobalt and bromine catalyst components for the purification procedure when the solvent for the purification procedure is obtained by partial displacement of the primary oxidation mother liquor. If the solvent for the purification process consists totally of fresh acetic acid (or a mixture thereof with water), then additional cobalt and bromine values must be added to the system. When sufficient cobalt and bromine values are not provided together with the residual mother liquor, these values may be provided in elemental, combined, or ionic form. For example, cobalt may be provided as inorganic cobalt salts, such as halides, nitrates, and oxides of cobalt, or as organic cobalt compounds, such as cobalt acetate, cobalt naphthenate, etc. The bromine component may be added as elemental bromine, hydrogen bromide, sodium bromide, ammonium bromide, potassium bromide, tetrabromoethane, benzyl bromide, 4-bromopyridine, etc. Hydrogen bromide and 4-bromopyridine are preferred bromine sources.

The cobalt component of the catalyst system of the present process can be present in a concentration of about 200 to 500 ppm, based on the concentration of cobalt in the reaction system. Preferably, the concentration of cobalt is about 300 to 400 ppm.

The bromine catalyst component is present in the purification process in a concentration of about 100 to 400 ppm, based on the total concentration of bromine (covalent and ionic) in the reaction system.

The catalyst system of the purification process of the present invention further comprises pyridine. It has been observed that the inclusion of pyridine in the catalyst system of the present purification process results in a more effective catalyst system. That is, a higher purity product is produced at a given set of reaction conditions if pyridine is added to the system.

The pyridine component of the catalyst system is preferably added directly to the purification process of the present invention (i.e., the secondary oxidation). The pyridine component of the catalyst system of the present invention can be in the form of pyridine per se or the form of a compound of pyridine which also provides other catalyst components to the purification process. A compound of this type which is preferred for use in the process of the present invention is 4-bromopyridine.

The pyridine component of the catalyst system of the present invention is present in an amount of about 0.1 to 5 moles per gram-atom of bromine. Preferably, pyridine is present in an amount of about one mole per gram-atom of bromine.

An especially preferred process in accordance with the present invention comprises contacting crude terephthalic acid which is produced by the oxidation of para-xylene with a mixture of nitrogen and oxygen comprising about 5 to 20% oxygen at a temperature of about 190° to 230° C. and a pressure of 1850 to 3600 kPa. The purification is conducted in the presence of a solvent which is preferably obtained by displacing about 80 to 90% of the mother liquor from the primary oxidation with fresh, wet, acetic acid containing about 5% water. The residual mother liquor from the primary oxidation supplies most, if not all, of the necessary cobalt catalyst component. The cobalt is present preferably in an amount of about 200 to 500 ppm. 4-Bromopyridine is preferably employed in the process in an amount such that about 100 to 400 ppm bromine is present in the reaction system.

The invention will be further illustrated by the following examples although it will be understood that these examples are included merely for purposes of illustration and are not intended to limit the scope of the invention.

EXAMPLES 1-7 & COMPARATIVE EXAMPLES 1-5

The following Examples and Comparative Examples were conducted in a batch process mode and were performed in a rocking titanium autoclave. The crude terephthalic acid (TPA), containing about 0.44% 4-carboxybenzaldehyde (4-CBA; an undesirable chain terminator and color-forming impurity), was prepared by the air oxidation of p-xylene with a cobalt/acetaldehyde catalyst. The crude TPA and catalyst were slurried in 95% acetic acid/5% water. The catalyst comprised the indicated concentration of cobalt, which was added as $Co(OAc)_2 \cdot 4H_2O$, the indicated concentration of bromine, and the indicated concentration of pyridine. When employed as the bromine source, the hydrogen bromide was in the form of a 48% aqueous HBr solution. In Comparative Examples 1-4, no pyridine was present; in Comparative Examples 5 and 6, neither pyridine nor bromine was present. The TPA/catalyst/solvent slurry was charged to the autoclave, pressurized to 500 psig with air, and heated to 200° C. After one hour, the autoclave was cooled and vented. The product was separated from the mixture by filtration, washed with acetic acid, and dried under 20 in. Hg vacuum at 80° to 100° C. The results are given below in Table I.

TABLE I

| Run | Catalyst | | | | |
| --- | --- | --- | --- | --- | --- |
| | Co (ppm) | Br (ppm) | Br source | Added Pyridine | 4-CBA (ppm) |
| Ex. 1 | 500 | 200 | HBr | 1 mole/mole HBr | 248 |
| Ex. 2 | 500 | 200 | HBr | 1 mole/mole HBr | 145 |
| Ex. 3 | 500 | 200 | 4-bromopyridine | — | 200 |
| Ex. 4 | 500 | 200 | 4-bromopyridine | — | 176 |
| Ex. 5 | 530 | 250 | 4-bromopyridine.HCl | — | 111 |
| Ex. 6 | 500 | 200 | 4-bromopyridine.HCl | — | 170 |
| Ex. 7 | 500 | 200 | 4-bromopyridine.HCl | — | 182 |
| Comp. Ex. 1 | 500 | 200 | HBr | — | 465 |
| Comp. Ex. 2 | 530 | 200 | HBr | — | 697 |
| Comp. Ex. 3 | 530 | 200 | HBr | — | 434 |
| Comp. Ex. 4 | 530 | — | — | — | 735 |

TABLE I-continued

| Run | Catalyst Co (ppm) | Br (ppm) | Br source | Added Pyridine | 4-CBA (ppm) |
|---|---|---|---|---|---|
| Comp. Ex. 5 | 530 | — | — | — | 595 |

The results of Table I clearly demonstrate the advantages provided by the process of the present invention. For example, in Comparative Examples 4 and 5, which illustrate prior art purification processes employing cobalt as the sole catalyst component, the purification process was effective in reducing the 4-CBA content of the product to a concentration on the order of 600 to 750 ppm. In Comparative Examples 1–3, wherein bromine in the form of aqueous HBr was added as a catalyst component, the process was effective in reducing the 4-CBA content to a concentration on the order of 450 to 700 ppm. In contrast to these results, the superior effectiveness of the process of the present invention is demonstrated by Examples 1–7 wherein pyridine is also employed as a catalyst component, either per se (Examples 1 and 2) or as 4-bromopyridine (Examples 3 and 4) or 4-bromopyridine hydrochloride (Examples 5–7). In these Examples, the 4-CBA content is reduced to a concentration on the order of 100 to 250 ppm. Thus, it is evident that the results of Examples 1–7 are dramatically and consistently better than those of the Comparative Examples which illustrate prior art processes.

The invention has been described in detail with particular reference to preferred embodiments thereof, but it will be understood that variations and modifications can be effected within the spirit and scope of the invention.

We claim:

1. In a process for the purification of crude terephthalic acid, said purification process comprising contacting said crude terephthalic acid with oxygen-containing gas at elevated temperature and pressure in the presence of a solvent containing at least one lower alkanoic acid and a catalyst system comprising cobalt, the improvement comprising employing in said catalyst system a bromine source and pyridine.

2. The process of claim 1 wherein said bromine source is HBr.

3. The process of claim 1 wherein said bromine source is 4-bromopyridine.

4. The process of claim 1 wherein said purification is conducted at a temperature of about 190° C. to 230° C.

5. The process of claim 1 wherein said purification is conducted at a pressure of about 1500 to 3600 kPa.

6. The process of claim 1 wherein said purification is conducted in the presence of about 200 to 500 ppm cobalt.

7. The process of claim 1 wherein said purification is conducted in the presence of about 100 to 400 ppm bromine.

8. The process of claim 1 wherein pyridine is present in an amount of about 0.1 to 5 moles per gram-atom of bromine.

9. The process of claim 1 wherein said oxygen-containing gas comprises a mixture of nitrogen and oxygen.

10. The process of claim 9 wherein said oxygen-containing gas comprises about 5 to 20% oxygen.

11. The process of claim 1 wherein said solvent comprises at least one alkanoic acid having 2 to 4 carbon atoms.

12. The process of claim 1 wherein said solvent is acetic acid.

13. In a process for the purification of crude terephthalic acid, said purification process comprising contacting said crude terephthalic acid with oxygen-containing gas at a temperature of about 190° C. to 230° C. and a pressure of about 1500 to 3600 kPa in the presence of a solvent containing acetic acid and a catalyst system comprising about 200 to 500 ppm cobalt, the improvement comprising employing in said catalyst system about 100 to 400 ppm bromine and about 0.1 to 5 moles of pyridine per gram-atom of bromine.

14. The process of claim 13 wherein said source of bromine is HBr.

15. The process of claim 13 wherein said source of bromine is 4-bromopyridine.

16. The process of claim 13 wherein said oxygen-containing gas comprises a mixture of nitrogen and oxygen, the oxygen comprising about 5 to 20% of said mixture.

17. The process of claim 13 wherein said solvent comprises a mixture of water and acetic acid having a water content of about 5%.

18. A process for the purification of crude terephthalic acid, said purification process comprising contacting said crude terephthalic acid with a mixture of nitrogen and oxygen comprising about 5 to 20% oxygen at a temperature of about 190° C. to 230° C. and a pressure of about 1500 to 3600 kPa in the presence of (1) a solvent comprising a mixture of water and acetic acid having a water content of about 5% and (ii) a catalyst system comprising about 200 to 500 ppm Co, about 100 to 400 ppm bromine, and about 0.1 to 5 moles of pyridine per gram-atom of bromine.

19. The process of claim 18 wherein said pyridine is present in an amount of about one mole per gram-atom of bromine.

20. A process for the purification of crude terephthalic acid, said purification process comprising contacting said crude terephthalic acid with a mixture of nitrogen and oxygen comprising about 5 to 20% oxygen at a temperature of about 190° C. to 230° C. and a pressure of about 1500 to 3600 kPa in the presence of (1) a solvent comprising a mixture of water and acetic acid having a water content of about 5% and (ii) a catalyst system comprising about 200 to 500 ppm Co and 4-bromopyridine in an amount such that about 100 to 400 ppm bromine is present in the reaction system.

* * * * *